United States Patent [19]

Reynolds et al.

[11] Patent Number: 5,678,557
[45] Date of Patent: Oct. 21, 1997

[54] ONE HAND PUSH BUTTON INTRAFLO

[75] Inventors: Gordon S. Reynolds, Bountiful; Robert H. Johnson, Sandy, both of Utah

[73] Assignee: Abbott Laboratories, Abbott Park, Ill.

[21] Appl. No.: 699,136

[22] Filed: Aug. 16, 1996

Related U.S. Application Data

[60] Continuation of Ser. No. 435,334, May 5, 1995, abandoned, which is a division of Ser. No. 173,549, Dec. 23, 1993, abandoned.

[51] Int. Cl.⁶ ..................................................... A61B 5/00
[52] U.S. Cl. ........................ 128/673; 128/675; 291/117; 137/923
[58] Field of Search ........................... 128/673, 675; 137/238, 902; 251/117, 320, 321, 903; 604/30, 32–4, 246–256

[56] References Cited

U.S. PATENT DOCUMENTS

| | | | |
|---|---|---|---|
| 4,291,702 | 9/1981 | Cole et al. | 128/673 |
| 4,696,305 | 9/1987 | Von Berg | 128/673 |
| 4,934,375 | 6/1990 | Cole et al. | 128/673 |

*Primary Examiner*—Robert L. Nasser
*Attorney, Agent, or Firm*—Neal D. Marcus; Ronald M. Anderson

[57] ABSTRACT

A flush device for an intravenous blood pressure monitoring system has a main body which includes a continuous flow channel and a fast flush channel. The continuous flow channel is integral with the main body and includes an inlet, a closed end which receives a laser drilled hole for fluid output, and an outlet. The continuous flow channel is separated from the fast flush channel by a median wall. An opening in the median wall is blocked by an elastomeric member disposed in an initial position in the fast flush channel. When the member is distended, the opening is unblocked, and fluid flow from the inlet to the outlet is through the fast flush channel. An alternative embodiment of the fast flush device has a tubular body with a capillary channel formed on an inner wall. An elastomeric member contained within the tubular body restricts flow to the capillary channel when the elastomeric member is in an initial position. When the elastomeric member is in a distended position fluid is allowed to overflow the capillary channel thus permitting either a fast flush flow between a source of medical fluid and the outlet on the fast flush device which is in fluid communication with the catheter.

7 Claims, 5 Drawing Sheets

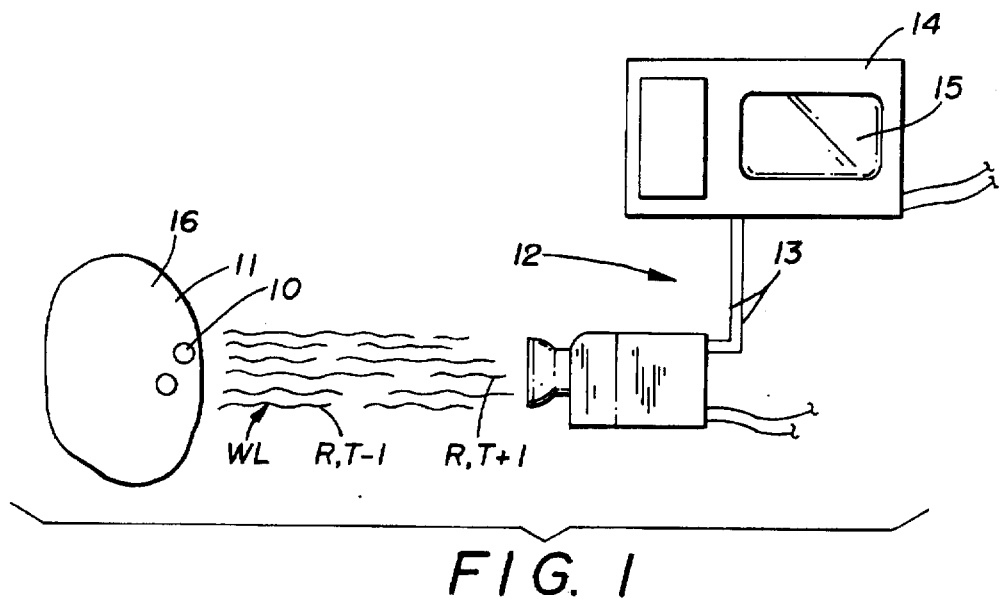
FIG. 1
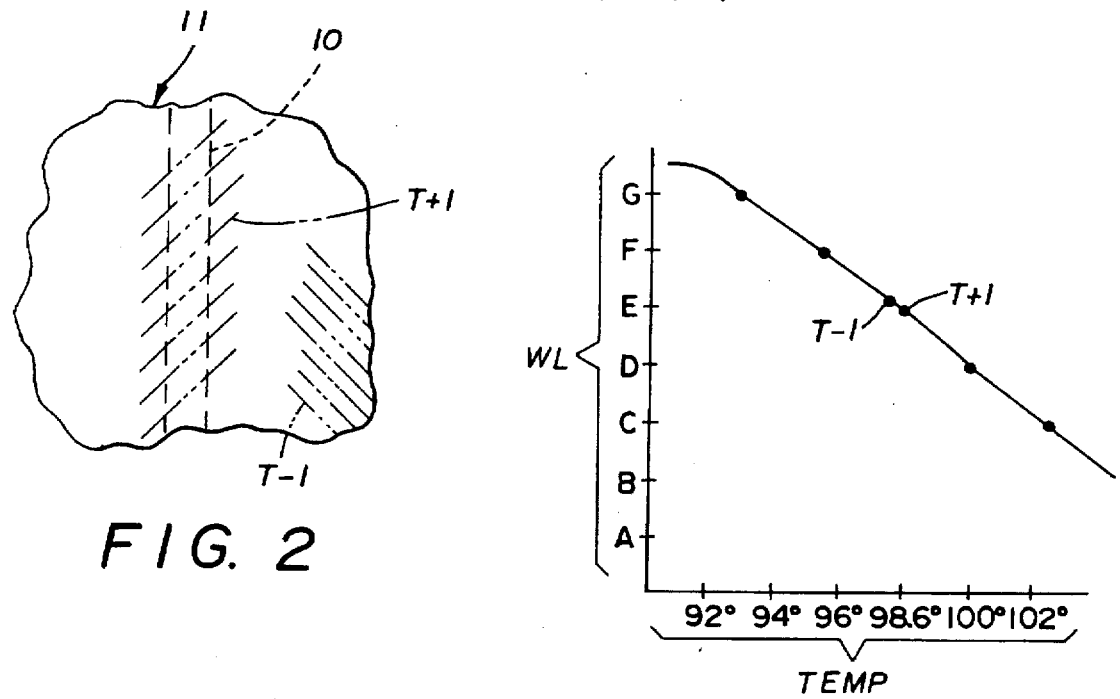
FIG. 2
FIG. 3
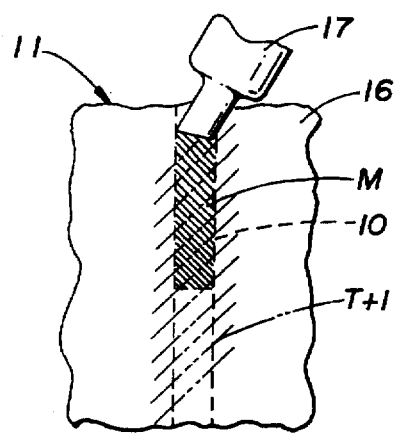
FIG. 4

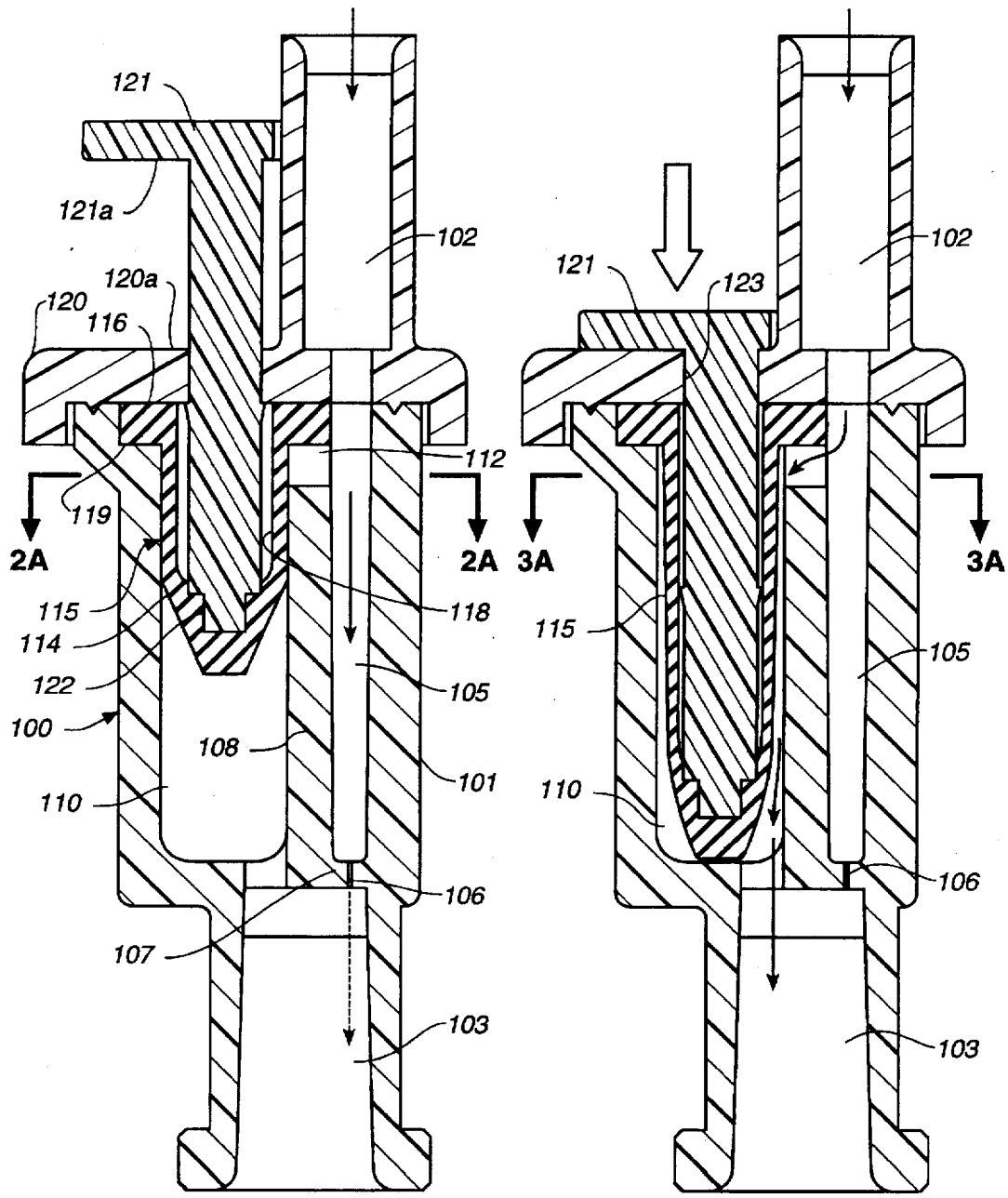
FIG._2  FIG._3

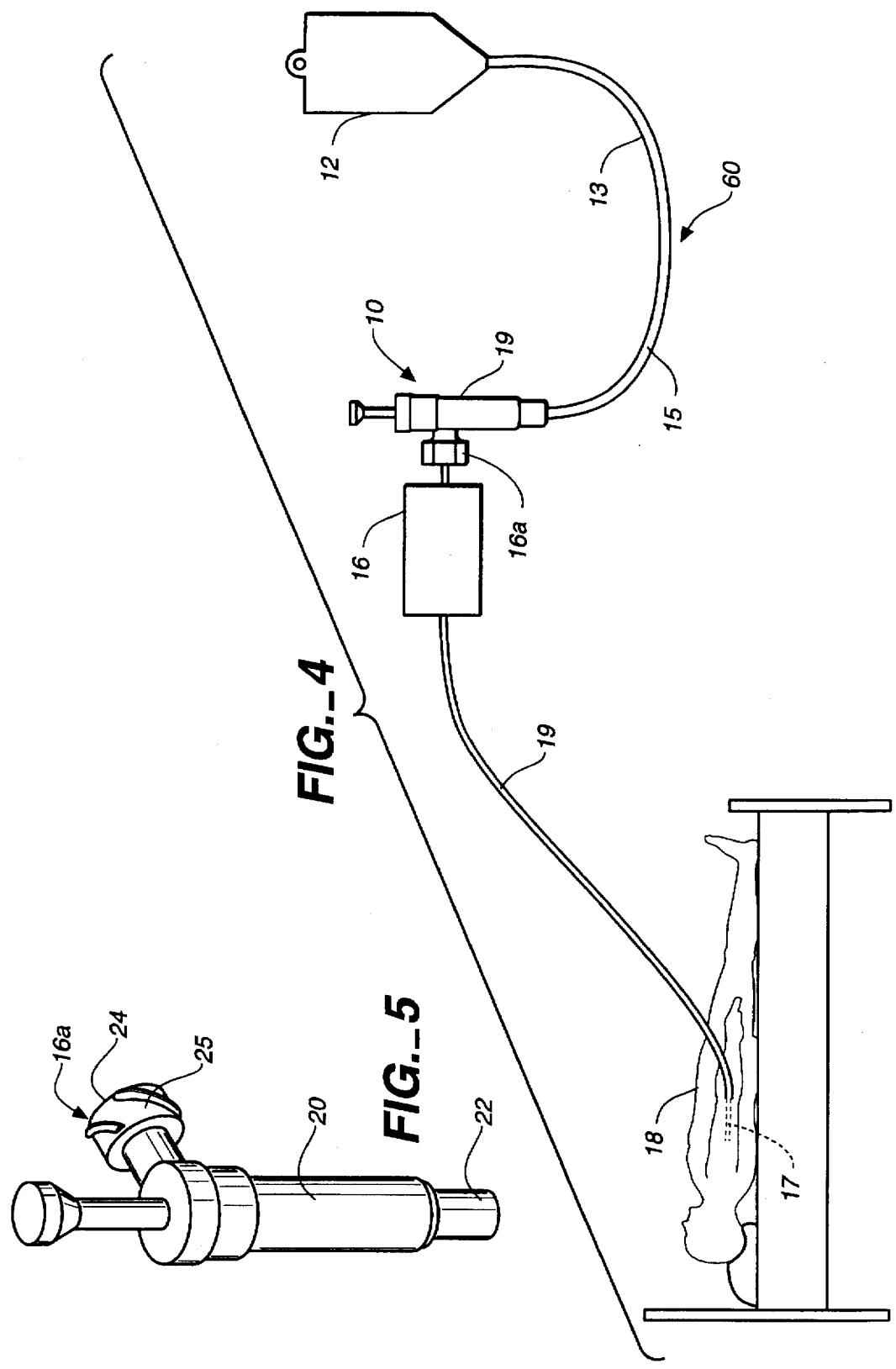

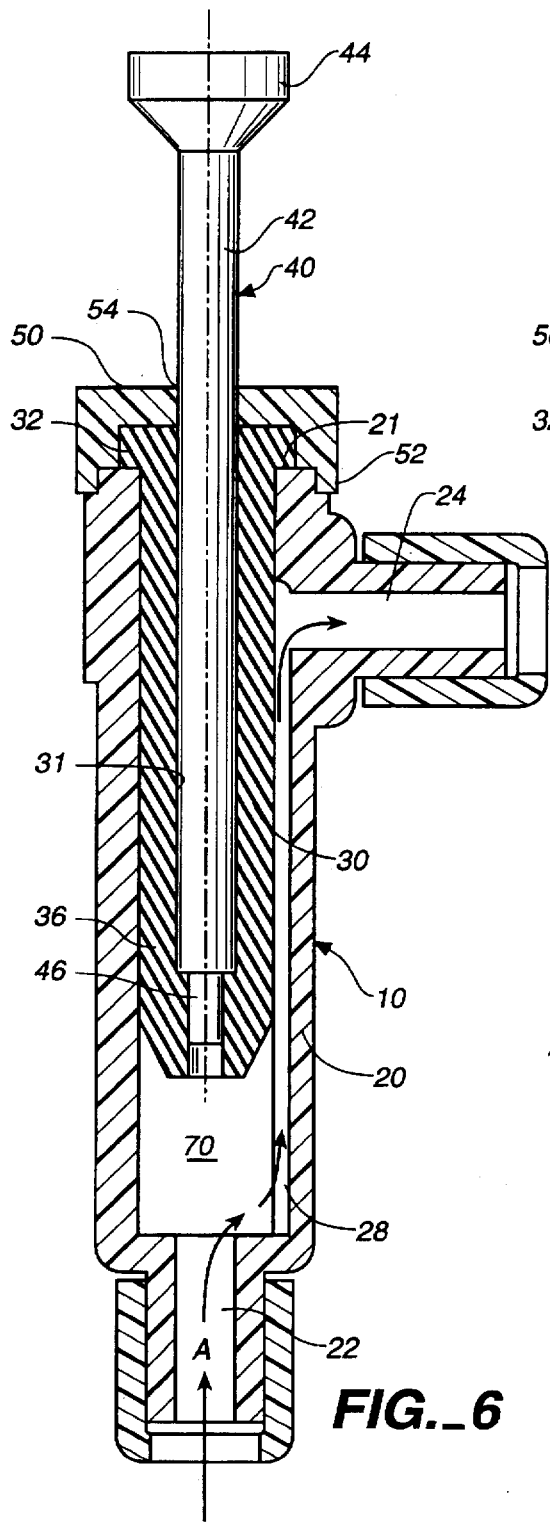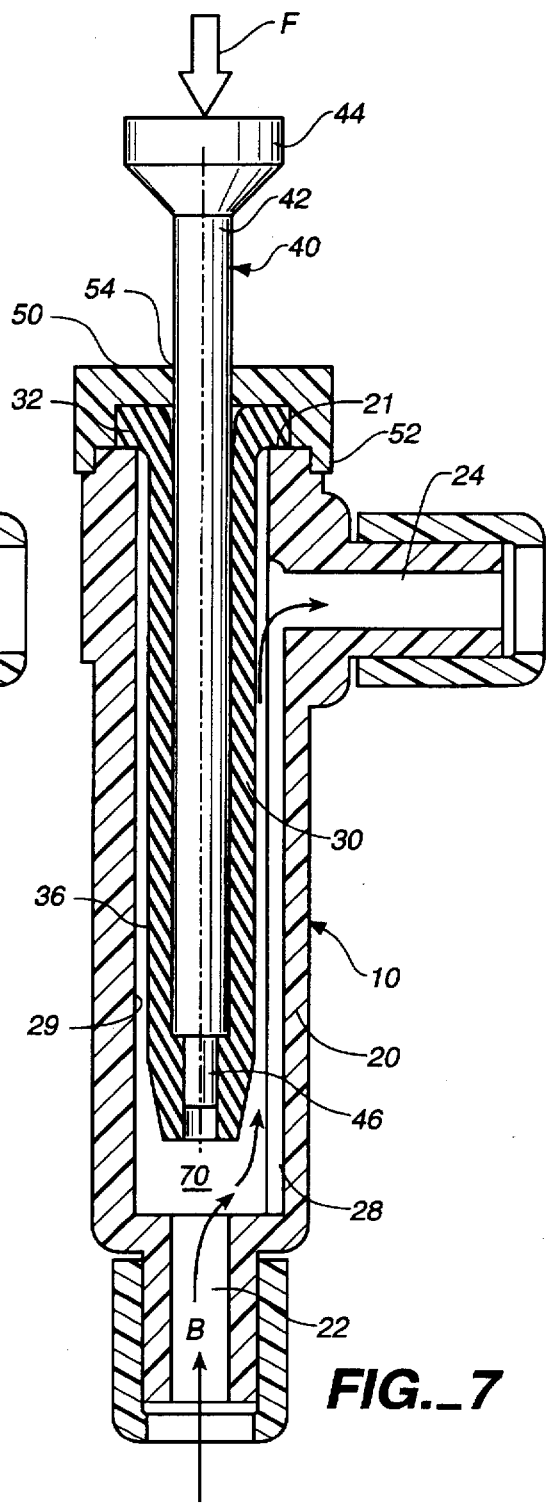

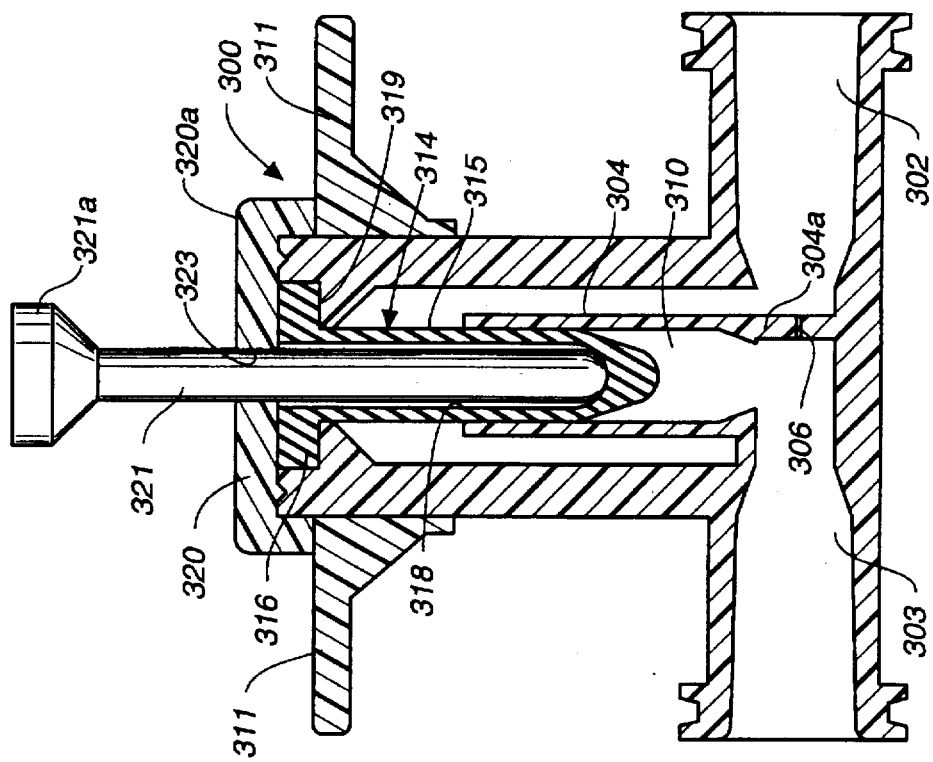
FIG._9
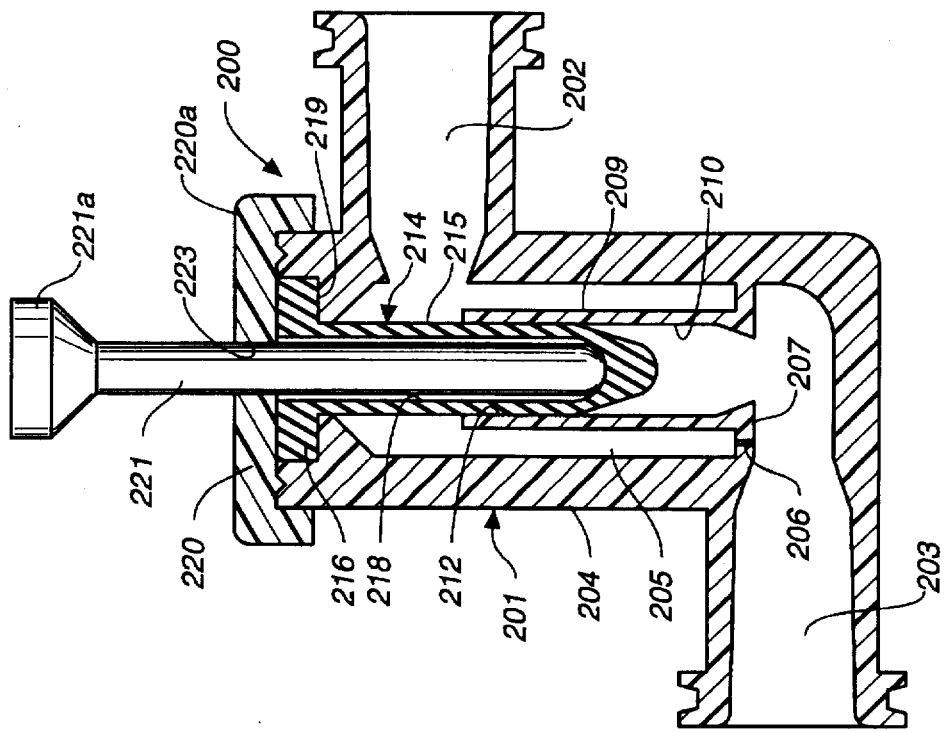
FIG._8

ONE HAND PUSH BUTTON INTRAFLO

This application is a file wrapper continuation application, based on prior application Ser. No. 08/435,334, filed May 5, 1995, now abandoned, which in turn is a divisional of prior application Ser. No. 08/173,549, filed Dec. 23, 1993, abandoned, the benefit of the filing date of which is hereby claimed under 35 U.S.C. §120.

BACKGROUND OF THE INVENTION

The present invention relates to a continuous fluid flow device; more particularly the present invention relates to a continuous fluid flow device which incorporates a fast flush capability.

In invasive blood pressure monitoring systems a catheter is placed within the vein or artery of a patient in order to sense the pressure of flowing blood. The sensed blood pressure is transmitted through the catheter to a pressure transducer which converts the sensed blood pressure into a pattern of electrical signals which in turn can be displayed on a visual monitor or recorded on a printed chart. If the end of the pressure sensing catheter becomes occluded or masked by the formation of a blood clot or thrombus, the blood pressure monitoring system will produce erroneous signals. Consequently, it is necessary to maintain a small continuous flow of medical liquid through the catheter to reduce the likelihood of formation of blood clots at the end of the catheter.

Additionally, it is desirable to purge air from the catheter on initial filling. This may easily be accomplished by providing a flush device which will allow a substantially larger bolus of fluid to fast flush the catheter. There is also a need to clear the catheter of blood or mixed blood and fluid after blood sampling procedures.

Representative of typical flush devices are those illustrated in U.S. Pat. No. 3,675,891 and U.S. Pat. No. 4,464,179. These two patents illustrate flush devices which utilize two separate channels for liquid flow. Specifically, there is a micro-bore continuous flow channel and a purge or fast flush channel. The continuous flow channel usually consists of a tube having a very small bore or capillary while the purge or fast flush channel is separate and apart from the continuous flow channel and is usually substantially larger in diameter.

Additionally the use of an elastomeric member to provide a blockage for the fast flush channel is shown in U.S. Pat. No. 4,696,305. Similar elastomeric members used in conjunction with a flush device are shown in U.S. Pat. Nos. 4,457,487 and 4,275,675.

In U.S. Pat. No. 4,696,305 a separate glass resistor is disposed in the continuous flow capillary channel. It would be desirable to eliminate additional components of the device such as the glass restrictor and to be able to provide a main body portion which includes a minimum of parts including a capillary bore laser drilled through the main body portion and a separate fast flush channel. It is also desirable to minimize the number of parts in the assembly.

As the continuous flow or capillary channel is extremely small, there is always the chance that clogging of the channel may result in a stoppage of the required continuous low flow of fluid. Such stoppages may be caused by particulate matter or impurities found in the medical liquid. There is, therefore, also a need in the art to provide a device that provides a single channel which may be easily cleared if a stoppage occurs.

It is also necessary to calibrate the dynamic response of the blood pressure monitoring system by sending an impulse or step function of pressure through the catheter and associated pressure tubing to provide a high quality square wave which can be visualized on the display monitor or printed chart. The oscillation and damping of the square wave by the various components in the pressure monitoring system are indicative of the frequency response of the system. Blood pressure measurement techniques are discussed at length in the article entitled "Direct Blood Pressure Measurement—Dynamic Response Requirements" by Reed M. Gardner, Ph.D., *Anesthesiology*, Vol. 54, No. 3, March 1981. Related articles include "Safety and Efficacy of Continuous Flush Systems for Arterial and Pulmonary Artery Catheters" by Reed M. Gardner, Ph.D., Edward L. Bond, Ph.D., and Justin L. Clark, Ph.D., *The Annals of Thoracic Surgery*, Vol. 23, No. 6, June 1977 and "Catheter-flush System for Continuous Monitoring of Central Arterial Pulse Waveform, by Reed M. Gardner, Homer R. Warner, Alan F. Toronto and Walter d. Gaisford, Dept. of biophysics and bioengineering, University of Utah, Latter-day Saints Hospital, Salt Lake City, Utah, *Journal of Applied Physiology*, Vol. 29, No. 6, December 1970. To the extent that the above articles will aid in the understanding of the present invention, they are incorporated herein by reference.

An alternative embodiment of the present invention provides a flush device with a single flow path for medical liquid. The single flow path both provides a continuous low flow of medical liquid to continuously purge the end of the catheter and also provides a larger flow path which enables a bolus of fluid to fast flush both the end of the catheter and the continuous flow channel.

SUMMARY OF THE INVENTION

In a main body position having an inlet and an outlet there is provided a micro bore or capillary continuous flow channel and a purge or fast flush channel. The continuous flow capillary channel is integral with the main body portion of the device and closed at one end, with the closed end having a very small bore or capillary drilled therethrough to permit continuous flow from the inlet to the outlet at a very slow rate.

The fast flush channel is separated from the continuous flow channel by a median wall therebetween. The fast flush channel is also substantially larger in size than the continuous flow channel. An opening at an upper end of the median wall enables passage of fluid from the inlet through the fast flush channel to the outlet. An elastomeric member installed in the fast flush channel blocks the opening in the median wall to block the flow of fluid from the inlet through the fast flush channel to the outlet in a first or blocking position of the member.

The elastomeric member has an internal bore which receives a plunger associated with the device. In the initial position of the member, the plunger is displaced from an upper wall of the main body position. When the plunger is depressed the elastomeric member is distended, moving the elastomeric member away from the opening in a median wall between the continuous flow channel and the fast flush channel thereby enabling fluid to flow from the inlet through the fast flush channel to the outlet in a fast flush position. It is particularly advantageous to provide a capillary opening in the main body portion at the end of the continuous flow channel to eliminate such members as a glass restrictor having a continuous micro-bore extending therethrough as shown in the above noted von Berg patent.

In an alternate configuration of the present invention, a flush device has a substantially tubular body. Formed on the inner wall of the tubular body is a capillary or continuous flow channel which runs the length of the tubular body. The capillary channel provides fluid communication between an inlet at one end of the tubular body and an outlet at the other end. Positioned within the tubular body is an elastomeric member which, in its initial position, sealingly engages the inner wall of the tubular body, particularly that portion of the inner wall of the tubular body adjacent the continuous flow channel. Continuous flow fluid from the inlet to the outlet is through the capillary channel formed on the inner wall of the tubular body.

When it is desired to provide a fast flush from a source of medical fluid through the flush device, a plunger contained with the elastomeric member is manually activated. The motion of the plunger causes the elastomeric member to move from an initial position to a distended position. This, in turn causes the elastomeric member to move away from the inner wall of the tubular body. Flow of medical fluid thereby overflows the continuous flow capillary channel as it is no longer restricted to the continuous flow channel by the elastomeric member. When the elastomeric member is returned to its initial position, the overflow position is terminated and flow is once again restricted to a slow flow rate through the continuous flow channel on the inner wall of the tubular body.

BRIEF DESCRIPTION OF THE DRAWINGS

A further understanding of the medical flush device of the present invention may be had by reference to the drawings wherein:

FIG. 1 is a perspective view of the flush device of the present invention;

FIG. 2 is a view, partially in section, taken along the lines 2—2 of FIG. 2 of the elastomeric body with the plunger disposed therein in an initial position;

FIG. 2A is a sectional view taken along the lines 2A—2A of FIG. 2;

FIG. 3 is a view similar to FIG. 2 wherein the plunger is depressed and the elastomeric body is distended;

FIG. 3A is a sectional view taken along the lines 3A—3A of FIG. 3;

FIG. 4 is a diagrammatic illustration of a system for the intravenous monitoring of the blood pressure in a patient including the device of an alternative embodiment of the present invention;

FIG. 5 is a perspective view of the alternative embodiment of the present invention;

FIG. 6 is a side elevational view partially in section of the alternative embodiment of the present invention in its configuration for providing a continuous or capillary flow;

FIG. 7 is a side elevational view partially in section of the alternative embodiment of the present invention in its configuration for providing a fast flush flow;

FIG. 8 is a side elevation, shown partially in section, of a second alternative embodiment of the flush device of the present invention; and FIG. 9 is a side elevation, shown partially in section, of a third alternative embodiment of the flush device of the present invention.

DETAILED DESCRIPTION OF THE EMBODIMENTS

The flush device of the present invention is best seen in FIGS. 1-3 wherein a device 100 comprises a main body portion 101 having an inlet 102 and an outlet 103. Disposed between the inlet 102 and the outlet 103 are a pair of fluid channels with a fluid channel 105 terminating in a capillary bore 106 which passes from the fluid channel 105 to the fluid outlet 103. The capillary bore 106 enables continuous fluid flow at a low or capillary rate from the inlet 102 to the outlet 103 through the capillary bore 106. The capillary bore 106 is drilled into a bottom wall 107 of the main body portion 101 below the fluid channel 105 as by laser drilling. The use of a laser drilled hole 106 eliminates the need for a glass restrictor or other object inserted in the channel 105 to provide a capillary bore therethrough.

A median wall 108 separates the continuous fluid flow channel 105 from a fast flush channel 110. An opening 112 in the median wall 108 connects the inlet 102 to the fast flush channel 110. An elastomeric member 114 disposed in the fast flush channel 110 blocks the opening 112 in an initial position to prevent fluid from flowing from the inlet 102 through the fast flush channel 110 to the outlet 103.

Elastomeric member 114 comprises a body 115 having an upper annular flange 116 and an internal bore 118. Flange 116 engages an annular shoulder extension 119 of the fast flush channel 110 and a cap 120 captures the annular flange 116 between the annular shoulder and the cap. Plunger 121 extends into the bore 118 of the elastomeric member 115 through an opening 123 in the cap 120 to seat in a shouldered seat 122 provided at the bottom of the interior of the bore of the member 114.

The operation of flush device 100 is as follows. Under a continuous fluid flow condition, there is fluid flow from the input 102 to the output 103 through the capillary bore 106 associated with the continuous flow channel 105. The continuous fluid flow rate is at a drip rate and substantially lower than the fluid flow rate when the fast flush channel 110 is open.

To open the fast flush channel 110, elastomeric member 114 is distended by depressing the plunger 121 until the bottom face 121a of the plunger 121 is in close proximity to or engages an upper face 120a of the cap 120 of the flush device 100. When the plunger 121 is depressed, the elastomeric body is distended to the position shown in FIG. 2, to enable fluid flow from the inlet 102 through the opening 112 in the median wall 108 through the fast flush channel 110 and through the outlet 103 at a fast flush rate.

In FIG. 4, the flush device of an alternative embodiment of the present invention is incorporated into a blood pressure monitoring system 60. The overall system 60 includes a pressurized infusion container 12 connected by a tube 13 to the flush device 10. The flush device 10 is also provided with a fitting 16a to which the transducer 16 is connected. The opposite end of transducer 16 is connected to the catheter 17 by tubing 19. In FIG. 4 the catheter 17 is advanced into the radial artery of a patient 18. The catheter could also be advanced through the jugular vein into the right heart chambers and to the pulmonary artery. The present invention is usable with various catheter systems wherein the catheter may be threaded through the various veins or arteries of the human body.

As may be seen best in FIG. 5, the flush device 10 of the alternative embodiment of the present invention includes three essential parts. Specifically, tubular member 20 is formed to contain a similarly shaped elastomeric member 30. Elastomeric member 30 has an internal bore 31 which receives a stem 42 of a plunger 40 which is used to distend the elastomeric member as shown in FIG. 7. The plunger 40 is directly inwardly to distend elastomeric member 30 to move away from the inner wall 29 of tubular member 20.

At the bottom of tubular member 20 is located inlet 22 which may be adapted for connection with various sizes of commonly used medical grade flexible tubing. As shown in FIG. 5, disposed opposite the inlet 22 is an outlet 24. Interposed between the inlet 22 and the outlet 24 is a capillary channel 28 provided in an inner wall of tubular member 20 as by laser drilling. The size of capillary channel 28 is exaggerated in FIGS. 6 and 7 for clarity.

Retaining elastomeric member 30 within the tubular member 20 is a cap 50. The cap 50 is in frictional engagement with the top 21 of the tubular member 20. The sides 52 of the cap 50 may be sonically welded or sealed to the top 21 of the tubular member 20. The cap 50 further includes an opening 54 which allows for the passage of the stem 42 when the cap 50 is in place on the tubular member 20. A flange 32 at the top of elastomeric member 30 is retained in position by the sealing of the cap 50 at the top 21 of the tubular member 20.

Formed on the top of the plunger 40 is an enlarged head section 44. An end 46 of the plunger 40 is in contact with the bottom 34 of the elastomeric member 30. As shown in FIG. 6, when the elastomeric member 30 is in an initial position, an annular side wall 36 of the elastomeric member 30 will be in sealing engagement with the inner wall 29 of tubular member 20 to provide a closure for the open side of the capillary channel 28.

As shown in FIG. 7, when the elastomeric member 30 is in a distended position, the side wall 36 of the elastomeric member is moved away from sealing engagement with inner wall 29. The movement of the member 30 away from the side of the tubular member 20 allows for increased flow through the tubular member 20 and overflows the capillary channel 28.

As may be best seen in FIG. 5, the outlet 24 further includes adaptations for luer fitments. In the preferred embodiment the outlet port 24 includes a male luer fitment 25.

The alternative embodiment device 10 is utilized in conjunction with an intravenous blood pressure monitoring system 60 as shown in FIG. 4. Such device allows for a continuous low flow of liquid to continually flush the end of catheter 17 indwelling within the body of the patient 18. When desired, however, it may be necessary to fast flush the end of the catheter 17 or provide a square wave for calibration by providing a bolus of fluid from the source of medical fluid 12. This bolus of solution is provided by the flush device of the present invention.

Normal or continuous low flow of fluid is provided by the flush device 10 of the present invention, when elastomeric member 30 is in an initial position as shown in FIG. 6. Therein, as may be seen by arrows labelled A, medical fluid enters the bottom of the device 10 and enters the capillary channel 28 which is formed on the inner wall 29 of the tubular member 20. Fluid then progresses through capillary channel 28 and out through outlet 24 thereby providing a continuous flow of fluid at a capillary or low flow rate to the end of the catheter 17 indwelling within the patient 18.

When it is desired to provide a bolus of solution to the end of the catheter for purging or calibrating with a square wave, force as indicated by arrow F in FIG. 6 is placed upon the enlarged head 44 of the plunger member 40. This force will cause plunger member 40 to move into the interior 70 of tubular member 20 and thus distend elastomeric member 30. The distending of elastomeric member 30 will cause it to move away from inner wall 29 thus breaking sealing engagement with the inner wall. Fluid, as may be seen by arrows B in FIG. 7 will now be allowed to progress through the inlet port 22, the overflow channel around the elastomeric member 30 and then pass out through the outlet 24 without being restricted by the capillary channel 28.

If a sampling device were interposed in line 19 between the patient 18 and the transducer 16, the flush device 10 would also protect the transducer 16 from damage due to over pressurization of the system 60 introduced by improper use of the sampling device; e.g., if the line to the patient were closed and an excessive pressure pulse was delivered to the transducer 16 from the sampling device in error.

The tubular member 20 and the plunger 40 may be formed from any suitable grade medical plastic. The elastomeric member 30 may also be formed of a rubber material which is compatible with medical fluids.

A second alternative embodiment of the flush device of the present invention is best seen in FIG. 8 wherein a device 200 comprises a main body portion 201 having an inlet 202 and an outlet 203. Disposed between the inlet 202 and the outlet 203 are a pair of fluid channels with an annular fluid channel 205 defined by outer wall 204 and inner wall 209. Fluid channel 205 terminates in a capillary bore 206 which passes from the fluid channel 205 to the fluid outlet 203. The capillary bore 206 enables continuous fluid flow at a low or capillary rate from the inlet 202 to the outlet 203 through the capillary bore 206. The capillary bore 206 is drilled into a bottom wall 207 of the fluid channel 205 as by laser drilling.

The annular wall 209 defines a fast flush channel 210. In an initial position, an elastomeric member 214 disposed in the fast flush channel 210 blocks an upper opening 212 to the flush channel 210 to prevent fluid from flowing from the inlet 202 through the fast flush channel 210 to the outlet 203.

Elastomeric member 214 comprises a body 215 having an upper annular flange 216 and an internal bore 218. Flange 216 engages an annular shoulder extension 219 of the flush device 200 co-extensive with the flush channel 210 and a cap 220 captures the annular flange 216 between the annular shoulder and the cap. Plunger 221 extends into the bore 218 of the elastomeric member 214 through an opening 223 in the cap 220 to engage the bottom of the bore of the member 214.

The operation of flush device 200 is as follows. Under a continuous fluid flow condition, there is fluid flow from the input 202 to the output 203 through the capillary bore 206 associated with the continuous flow channel 205. The continuous fluid flow rate is at a drip rate and substantially lower than the fluid flow rate when the fast flush channel 210 is open.

To open the fast flush channel 210, elastomeric member 214 is distended by depressing the plunger 221 until a head portion 221a of the plunger is in close proximity to or engages an upper face 220a of the cap 220 of the flush device 220. When the plunger 221 is depressed, the body 215 of the elastomeric member 214 is distended, to enable fluid flow from the inlet 202 through the fast flush channel 210 and through the outlet 203 at a fast flush rate.

As third alternative embodiment of the flush device of the present invention is best seen in FIG. 9 wherein a flush device 300 comprises a main body portion 301 having an inlet 302 and an outlet 303. Disposed between the inlet 302 and the outlet 303 is an annular wall 304 having a lower extension 304a disposed between the inlet 302 and the outlet 303. A capillary bore 306 laser drilled through wall 304a enables fluid flow at a capillary rate from the inlet 302 to the outlet 303.

The annular wall 304 defines a fast flush channel 310. Gripping members 311 are disposed on opposite sides of the wall 304. In an initial position, an elastomeric member 314 disposed in the fast flush channel 310 blocks an upper opening 312 to the fast flush channel 310 to prevent fluid from flowing from the inlet 302 through the fast flush channel 310 to the outlet 303.

Elastomeric member 314 comprises a body 315 having an upper annular flange 316 and an internal bore 318. Flange 316 engages an annular shoulder extension 319 of the flush device 300 co-extensive with the flush channel 310 and a cap 320 captures the annular flange 316 between the annular shoulder and the cap. Plunger 321 extends into the bore 318 of the elastomeric member 314 through an opening 323 in the cap 320 to engage the bottom of the bore of the member 314.

The operation of flush device 300 is as follows. Under a continuous fluid flow condition, there is fluid flow from the input 302 to the output 303 through the capillary bore 306 in wall 304a. The continuous fluid flow rate is at a drip rate and substantially lower than the fluid flow rate when the fast flush channel 310 is open.

To open the fast flush channel 310, elastomeric member 314 is distended by engaging gripping members 311 and a head portion 321a of the plunger 321 to depress the plunger 321 until the head portion 321a of the plunger 321 is in close proximity to or engages an upper face 320a of the cap 320 of the flush device 300. When the plunger 321 is depressed, the body 315 of elastomeric member 314 is distended to enable fluid flow from the inlet 302 through the fast flush channel 310 and through the outlet 303 at a fast flush rate.

There is now provided by the present invention a flush device which will allow continuous low flow of fluid from a fluid source to an indwelling blood pressure monitoring catheter, allow for a continuous flow of medical fluid through the catheter when desired and provide pressure relief to protect the transducer in a blood pressure monitoring system.

Although the flush device of the present invention has been described with respect to its preferred embodiment hereof, it is, however, not intended that the present fast flush device be limited to such embodiment only, but rather it should be defined by the scope of the appended claims.

We claim:

1. A flush device for an intravascular blood pressure monitoring system comprising:
    a tubular body having an outer wall that defines an internal chamber;
    a capillary channel comprising a slit formed in an inner surface of the outer wall and open to the internal chamber along the inner surface of the outer wall, said slit extending generally parallel to a longitudinal axis of said tubular body and providing a path for restricted flow through the tubular body;
    an inlet in fluid communication with the internal chamber of said tubular body and disposed at one end of said tubular body;
    an outlet in fluid communication with the capillary channel and the internal chamber of said body and disposed adjacent an opposite end of said tubular body from said inlet;
    an elastomeric member, which sealingly engages the inner surface of the outer wall of said tubular body in an initial position in which the elastomeric member covers at least a portion of the slit that limits fluid flow through the tubular body, said elastomeric member being displaced from said inner surface of the outer wall and uncovering the slit when the elastomeric member is in a distended position; and
    a plunger associated with said elastomeric member disposed to distend said member within the internal chamber of said tubular body from the initial position to the distended position;
    wherein when said elastomeric member is in sealing engagement with said inner surface of the outer wall, said capillary channel conveys a continuous low flow of a fluid from said inlet to said outlet, and when said elastomeric member is moved out of sealing engagement with said inner surface of said outer wall and the slit, a fast flush flow of the fluid is provided through the internal chamber, generally overflowing and bypassing the path defined by said capillary channel.

2. The flush device as defined in claim 1, wherein said inlet includes means for engaging flexible tubing.

3. The flush device as defined in claim 1, wherein said outlet has a luer fitting.

4. The flush device as defined in claim 1, wherein said plunger has a longitudinal stem, one end of said stem being in contact with said e other end of said stem having an enlarged head portion.

5. The flush device as defined in claim 4, further including a cap disposed at one end of the internal chamber, having a central orifice, said cap retaining said elastomeric member within said tubular body, said stem of said plunger passing through said central orifice.

6. A flush device for an intravascular blood pressure monitoring system comprising:
    (a) a housing having an inner surface that defines a chamber within said housing, said chamber having an inlet port for receiving a fluid and an outlet port through which fluid passes from the housing;
    (b) a slit formed in the inner surface, said slit having a side open to the chamber along a length of the slit and being in fluid communication with the inlet port and the outlet port to provide a capillary flow path through the housing between the inlet port and the outlet port;
    (c) an elastomeric member disposed within the chamber and extending along the longitudinal axis of the housing, said elastomeric membrane being in sealing contact with the inner surface of the housing and sealingly covering at least a portion of the side of the slit when the elastomeric membrane is relaxed and not distended, fluid flow through the housing being then limited to the capillary flow path defined by the slit; and
    (d) a plunger extending into the housing and into a cavity formed within the elastomeric member, said plunger having a head disposed outside the housing that is adapted to receive a force applied by a user causing the plunger to distend the elastomeric member into the chamber, thereby forcing the elastomeric member away from both the inner surface and the slit to enable a fast flushing flow of the fluid through the chamber from the inlet port and out the outlet port, said fast flushing flow of the fluid bypassing the capillary flow path defined by the slit.

7. A flush device for an intravascular blood pressure monitoring system comprising:
   (a) a tubular body in which is disposed a chamber, said tubular body having an inlet port and an outlet port in fluid communication with the chamber, for respectively conveying a fluid into the chamber and out of the chamber, said chamber comprising both a fast flushing flow path and a capillary flow path through the tubular body between the inlet port and the outlet port, said capillary flow path being formed as an open channel extending along an inner surface of said chamber;
   (b) an elastomeric member disposed within the chamber so as to block the fast flushing flow path through the chamber when the elastomeric member is in an initial position in which the elastomeric member covers at least a portion of the open channel formed along the inner surface of the chamber; and
   (c) means for enabling a user to selectively activate a fast flushing flow of the fluid through the chamber by distending the elastomeric member from the initial position into a distended position in which it is not in sealing contact with the inner surface of the chamber, so as to open the fast flushing flow path and uncover the open channel formed in the inner surface of the chamber, said fast flushing flow of the fluid thus bypassing the capillary flow path.

* * * * *

UNITED STATES PATENT AND TRADEMARK OFFICE
CERTIFICATE OF CORRECTION

PATENT NO. : 5,678,557
DATED : October 21, 1997
INVENTOR(S) : Reynolds et al.

It is certified that error appears in the above-identified patent and that said Letters Patent is hereby corrected as shown below:

Column 8, line 27, change "e" to --elastomeric member and the--.

Signed and Sealed this

Twelfth Day of May, 1998

Attest:

BRUCE LEHMAN

Attesting Officer

Commissioner of Patents and Trademarks